Figure 4:
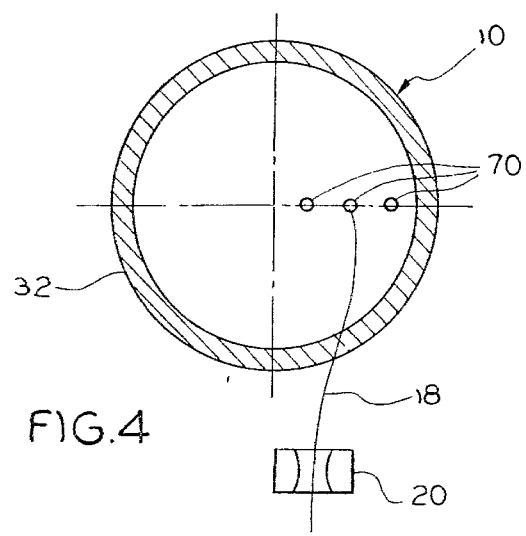

United States Patent [19]

Orlowski et al.

[11] 4,251,633
[45] Feb. 17, 1981

[54] MULTI-STAGE CONTINUOUS SYSTEM FOR PRODUCTION OF HETEROPOLYSACCHARIDES

[76] Inventors: David C. Orlowski, 190110 Sixth Ave., West Milan, Ill. 61264; Brooks D. Church, 326 W. Caley Dr., Littleton, Colo. 80120

[21] Appl. No.: 48,013

[22] Filed: Jun. 11, 1979

[51] Int. Cl.³ .............................................. C12M 1/40
[52] U.S. Cl. ................................. 435/288; 210/500.2; 435/104; 435/910; 435/813
[58] Field of Search ............... 435/287, 288, 299, 313, 435/317, 802, 803, 813, 819, 104, 910; 210/19, 22 R, 500 M

[56] References Cited

U.S. PATENT DOCUMENTS 2,734,015   2/1956   Wettstein et al. ............... 435/288 X

*Primary Examiner*—Robert J. Warden

[57] ABSTRACT

A multi-stage continuous system for producing heteropolysaccharides. The system comprises: a fermentation stage consisting of an outer enzyme/nutrient containing chamber in which a membrane microbial growth chamber is movably mounted, the growth chamber being arranged to continuously produce *Xanthomonas campestris* cells in the late exponential-early stationary phase of growth and transfer polymerizing exo-enzymes and cell lysate therefrom into the surrounding medium of the enzyme/nutrient chamber and to retain the *Xanthomonas campestris* cells; and a polymerization state consisting of at least one module to receive the exo-enzymes and cell lysate from the fermentation stage to produce heteropolysaccharides.

8 Claims, 6 Drawing Figures

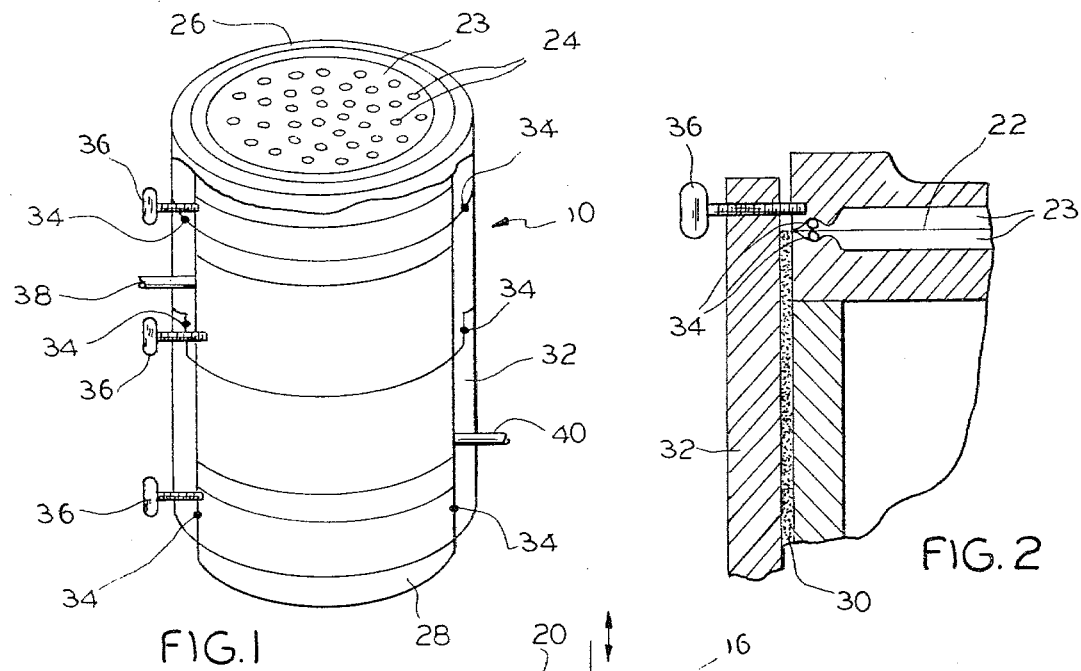
FIG. 1
FIG. 2
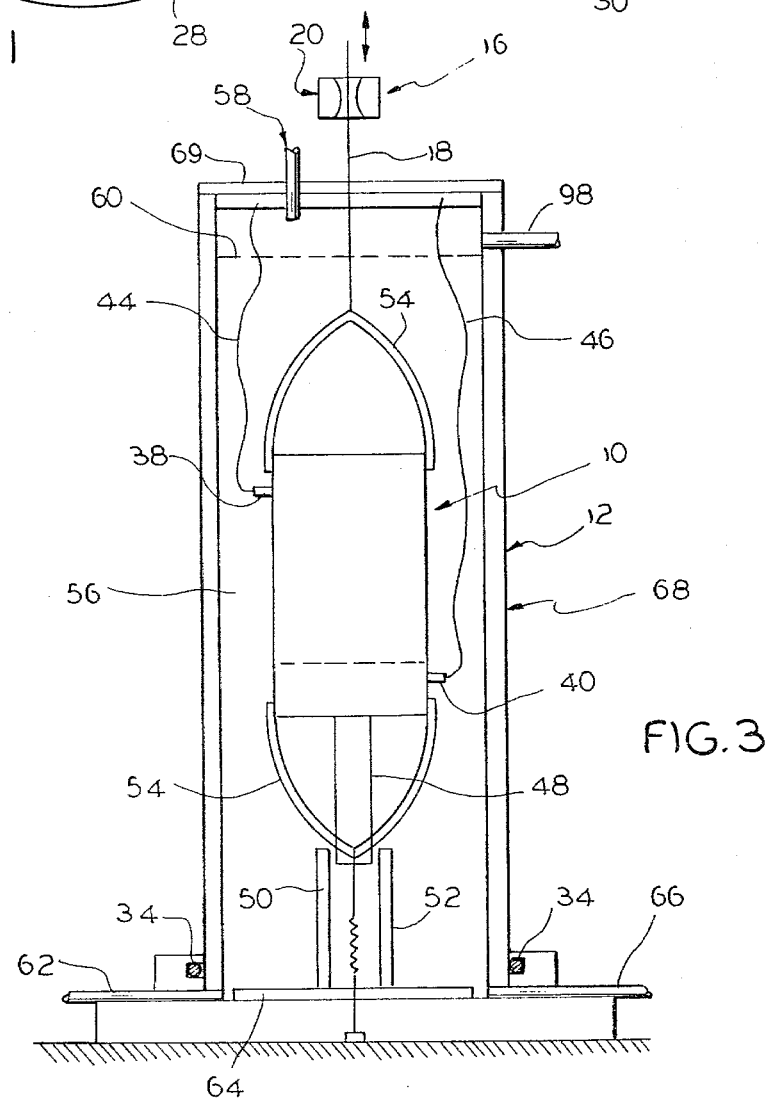
FIG. 3

MULTI-STAGE CONTINUOUS SYSTEM FOR PRODUCTION OF HETEROPOLYSACCHARIDES

BACKGROUND OF THE INVENTION

This invention relates to a continuous process for producing heteropolysaccharides, and more particularly to a multi-stage continuous system for producing heteropolysaccharides.

In recent years considerable interest has been exhibited in heteropolysaccharides produced by the bacterial fermentation of carbohydrates. This interest has been greatly increased by the discovery that certain heteropolysaccharides formed by biochemical synthesis have properties which permit their use as thickening agents for water used in secondary recovery operations carried out in the petroleum industry, and also as food-grade ingredient for thickening such products as salad dressing. It has been found that some of these materials added to water or brine in suitable concentrations produce viscous solutions which are relatively stable under the conditions which prevail in subsurface oil reservoirs and food substances. By utilizing a solution of controlled viscosity in place or in addition to the water or brine normally employed in waterflooding projects, a favorable mobility ratio between the oil in the reservoir and the liquid used to displace it can be obtained. The tendency of the displacing medium to channel through highly permeable sections of the reservoir without displacing oil from the less permeable sections is greatly decreased. Viscous forces which normally reduce the displacement efficiency in portions of the reservoir through which the displacing medium actually passes are more readily overcome. As a result of these effects, the use of water or brine containing polysaccharide thickening agents generally permits the recovery of significantly greater quantities of oil during waterflooding than can be removed with water or brine alone.

A particularly effective polysaccharide for use as a thickening agent during oil field waterflooding operations is the heteropolysaccharide produced by the growth and enzymatic action of bacteria of the genus Xanthomonas upon sugar, starches and similar carbohydrates. This material is more commonly know as "Xanthan gum". Studies and comparitive tests have shown that this material, a polymer containing mannose, glucose, glucuronic acid salts, and acetyl radicals has much greater thickening power than dextran and similar polysaccharides and hence can be used in significantly lower concentrations than the other materials. It is effective in both fresh water and brine and has excellent high temperature stability characteristics.

Although the heteropolysaccharide, i.e., "Xanthan gum", has superior qualities and characteristics for use in the petroleum industry, the total capacity for its production is far below its requirement. In fact, the present capability for its production is less than 20% of its estimated requirement in the near future.

Thus, there is a need for processes and systems which will greatly increase the production of the heteropolysaccharides to satisfy the requirements in the petroleum industry. In addition, there are other industries which require significant amounts of "Xanthan gum" such as the food industry where it is used as a stabilizing agent and/or thickener.

The present invention, as described below, is intended to satisfy this need by providing a continuous system for the production of heteropolysaccharides, i.e., Xanthan gum, which is efficient, effective, and relatively cell-free.

SUMMARY OF THE INVENTION

This invention provides a multi-stage cell-free continuous system for producing heteropolysaccharides. The continuous system comprises:

(a) a fermentation stage consisting of an outer enzyme/nutrient containing chamber in which a membranous microbial growth chamber is movably mounted, said growth chamber being arranged to continuously produce *Xanthomonas campestris* cells in the late exponential-early stationary phase of growth and transfer polymerizing exo-enzymes and cell lysate therefrom into the surrounding medium of said enzyme/nutrient chamber and to retain said *Xanthomonas campestris* cells; and (b) a polymerization stage consisting of at least one module to receive said exoenzymes and cell lysate from said fermentation stage to produce said heteropolysaccharides.

The membranous growth chamber is connected to an eccentric drive means which moves the growth chamber in a manner to facilitate transfer of the exo-enzymes and cell lysate therefrom thru the membranes into the surrounding nutrient/enzyme medium, and to produce in the growth chamber a Bernoullian presentation pressure on a forward membrane with an equal and opposite negative pressure on a rear membrane surface, thereby retaining the *Xanthomonas campestris* cells in the growth chamber.

BRIEF DESCRIPTION OF THE DRAWINGS

The advantages of the present invention will be more fully understood when considering the following detailed description in conjunction with the drawings, in which:

FIG. 1 is a perspective view of the membranous microbial growth chamber of the present invention;

FIG. 2 is a partial sectional view of the membranous microbial growth chamber of FIG. 1;

FIG. 3 is an elevational view of the Fermentation Stage according to the present invention;

FIG. 4 is a schematic view of the connection of the eccentric drive means to the membranous microbial growth chamber illustrated in FIG. 1; and FIG. 5 is a schematic view of the pattern of the air sparge line as arranged in the enzyme/nutrient containing chamber of the present invention.

FIG. 6 is a perspective view of one of the modules of the polymerization stage.

DETAILED DESCRIPTION OF PREFERRED EMBODIMENTS

The present invention provides a multi-stage continous system for producing heteropolysaccharides. The system as illustrated in FIG. 3, has a fermentation stage which consists of a membranous microbial growth chamber 10 which is movably mounted in an outer, nutrient/enzyme containing chamber 12. The growth chamber 10 is caused to move by eccentric drive means 16 which is connected by a cord 18 passed through a guide 20 to the growth chamber 10.

Referring to FIGS. 1 and 2, the growth chamber 10 is illustrated in detail. The chamber 10 has a membrane 22 on its top and bottom (not shown). The membranes 22 set in membrane supports 23 have a random pattern of holes of micron size or smaller. The membrane supports 23 also have holes 24 of a larger size. The membrane supports are recessed and secured by covers 26 and 28. The covers are secured with lugs (not shown) to the growth chamber 10.

The membrane supports 23 are supported on both sides by contacting members (sidewalls) 30 (FIG. 2) which may be a metal, plastic, or other material of rigid or semi-rigid or flexible structure to ensure longevity of the membranes 22. The membranes 22 and contacting members 30, are contained by limiting walls 32. The walls 32 are secured to the contacting members 30 and the membranes 22 by an "O" ring 34 and lock pin 36 arrangement as illustrated if FIG. 2. The "O" ring 34 is smooth all over and is loosely fitted so that the porous contacting members 30 are not crushed.

The growth chamber 10 (FIGS. 1 and 3) has an inlet 38 for inoculation of *Xanthomonas campestris* cells and an outlet 40 for continous removal of bacterial cells to the outside environment. The emitting or transferring of the polymerizing exo-enzymes and cell lysate produced by the cell population in the growth chamber, into the nutrient/enzyme medium of the outer chamber 12 (FIG. 3) is through the membranes 22. The inlet 38 and the outlet 40 have flexible tubing 44 and 46 respectively, attached for constant continuous removal and addition of *Xanthomonas campestris* cells. Tubing 44 and inlet 38 are also used to provide additional oxygen supply and mixing of cells.

As illustrated in FIG. 1, the covers 26 and 28 are set within the outer walls 32. The membranes 22 are slightly recessed from about 0.020 to about 0.050 inches.

As shown if FIG. 3, the growth chamber 10 is movably mounted in the outer chamber 12 by means of a guide plunger 48 in a guide tube 50 in which a stainless steel spring 52 is positioned. The growth chamber 10 is placed in the outer chamber 12 by means of handles 54 secured to its top and bottom. Initially, the growth chamber 10 is placed in a nutrient growth medium 56 which is fed through inlet 58 to a level 60 above the growth chamber 10.

The medium 56 is moved around in the chamber 12 by air that is fed through inlet 62 into a sparge line 64. With the combination of the guide plunger 48, i.e., a telescoping yaw control guide, on the gravitational side of the growth chamber 10 and the air inlet 62 a positive displacement (PD) pump action is provided to assure the absence of any accumulation on the floor of the outer chamber 12. Heteropolysaccharides may be removed through drain tube 66.

The outer chamber 12 may have walls 68 and a cover 69 of standard acrylic. The enzyme production vessel 12, as shown in FIG. 3, is secured to a base by "O" ring 34 seals. The outer chamber, as illustrated, is substantially larger than the growth chamber, i.e., from about five (5) to about seven (7) times as large in volume.

Figure 6:
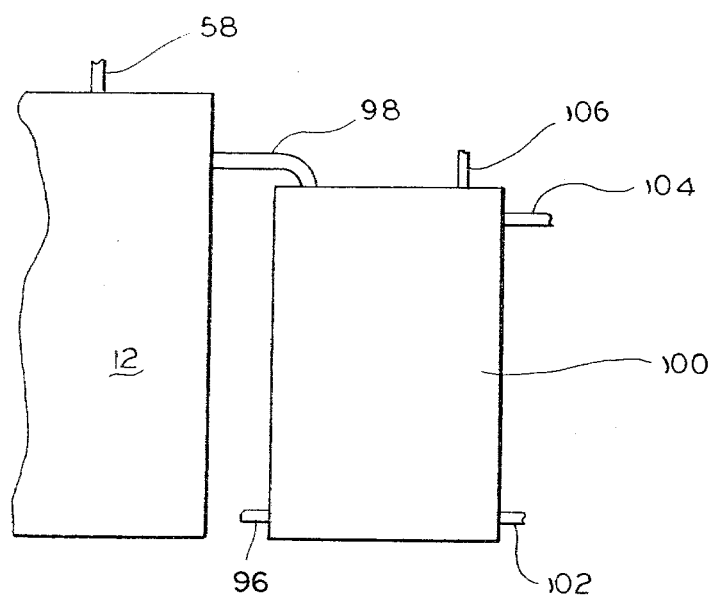

The cell-free polymerization stage consists of modules or chambers 100 (FIG. 6) similar to the outer chamber 12. The difference being that such modules do not contain a growth chamber 10. The polymerization stage consists of at least one such module. The number of polymerizing modules used in the operation corresponds to the length of time required to produce the "Xanthan gum" (i.e., heteropolysaccharides) of a desired viscosity. For example, where the desired viscosity is about 6,000 cp, one module is used, whereas when the desired viscosity is about 18,000 cp, two or more modules are used.

The polymerization module 100 received enzyme/lysate from outer chamber 12 through tube 98. Air enters module 100 through inlet 96 in a similar fashion as though fed through air inlet 62. The air insures the continued movement and mixing of the enzyme/lysate during polymerization. After polymerization is complete, the heteropolysaccharides are reviewed through drain tube 102. In the event additional modules are required for greater viscosity, additional modules may be set up to be fed through an outlet such as tube 104. During the whole polymerization there is a constant feeding of nutrient or enzyme substrate of the system through tubes such as 106.

The growth chamber 10 is caused to move by an eccentric drive means which consist of an eccentric drive, e.g., motor (not shown), a nylon cord 18 passed through a guide 20 and connected to one of the alternate drive posts 70 of the growth chamber (FIG. 4). The eccentric drive is a DC drive with a variable speed ranging from about 0 to about 20 RPM.

The eccentric drive means moves the growth chamber 10 in a manner to promote the transfer of nutrient from chamber 12 and exo-enzymes from growth chamber 10 across the membrane 22 surfaces. The exo-enzymes being produced from the *Xanthomonas campestris* cells in the growth chamber 10 are transferred through the membrane 22 into the surrounding medium 56 which initially was only a nutrient medium. With the continued cell growth and movement of chamber 10 the medium is supplemented with enzymes and cell lysate. The eccentric drive also provides for a variable, programmable frequency of movement (oscillation) while also allowing variable amplitude of predictable, sine wave description whereas any other method of inducing liquid transfer in and out of the growth chamber would likely be less gentle and prone to shock loading of the enzyme/nutrient transfer membrane.

In addition, the movement of the growth chamber 10 in the growth nutrient 56 produces a Bernoullian presentation pressure on a forward membrane with an equal but opposite negative pressure on a rear membrane surface, thereby retaining the *Xanthomonas campestris* cells in the growth chamber 10.

The growth chamber with its inlet 38 and outlet 40 arrangement, membrane surfaces 22 and filter supports 23 provide for a rapid and complete removal, replacement, and/or modification of the microbial mass (i.e., *Xanthomonas campestris* cells) in the growth chamber 10 from the fermentation state during the continuous operation of the present multi-stage system.

Moreover, the present growth chamber 10 and the overall fermentation and polymerization system as described above, provide for monitoring and sampling the bacterial cell-free, enzymeladen medium during its transfer to or from (or in) the intermediate stages, e.g., polymerization modules. Accordingly, bacteria-laden medium from membrane failure can be alternately directed to avoid mixing with a bacteria-free product.

Figure 5:
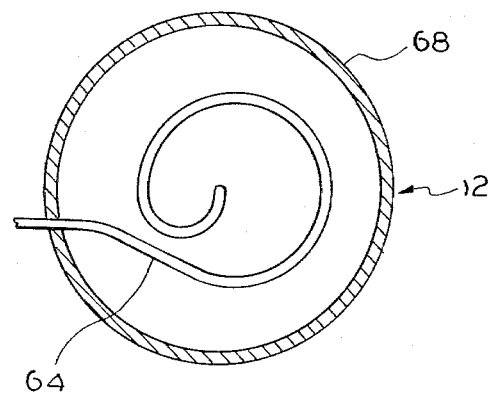

Referring to FIG. 5, the air sparge line 64 is shown in a pattern that it may be arranged. The sparge line 64 is arranged on the floor of the enzyme production vessel 12 and the polymerization modules.

The overall operation of the present continuous cell-free multi-stage system consists initially of inoculating *Xanthomonas campestris* cells in the near stationary phase of growth into the growth chamber 10 in which polymerizing exo-enzymes are produced. The exo-enzymes cell lysates are transferred by means of the movement caused by the eccentric drive means 16 from the growth chamber 10 through a membrane 22 into the surrounding medium of the outer chamber 12. The exo-enzymes cell lysates and the surrounding nutrient are transferred by a positive displacement (PD) pump action (created in the outer chamber) from the enzyme production vessel 12 to a polymerization module where the heteropolysaccharide (i.e., Xanthan gum) is produced.

The heteropolysaccharide described above is normally produced by inoculating a medium containing from about 1 to about 5 percent by weight of a suitable carbohydrate, organic nitrogen sources, dipotassium hydrogen phosphate and appropriate trace elements with an organism of the genus Xanthomonas and then permitting the culture to incubate at about 28° C., a pH of 7.2, under aerobic conditions for a period of about three to four days. Carbohydrates which may be employed in this manner include glucose, fructose, maltose, sucrose, lactose, galactose, soluble starch, e.g., corn starch and the like. Specific Xanthomonas organisms which may be used to produce heteropolysaccharides include *Xanthomonas campestris, Xanthomonas phaseoli, Xanthomonas malvacearum, Xanthomonas translucens, Xanthomonas carotae, Xanthomonas hederaz, Xanthomonas papavericola, Xanthomonas begoniae, Xanthomonas incanae, Xanthomonas vasculorum* and *Xanthomonas vesicatoria.*

At the end of this continuous run, the crude polymer formed in the enzyme medium is separated from the bacterial cells and does not require classical separation steps such as dilution, centrifugation or filtration and thereafter isolation and purification by precipitation with methanol, ethanol, acetone or a similar reagent. After drying, the heteropolymer is recovered as a light fluffy power which may be slightly tinted by colored materials from the culture medium.

I claim:

1. A multi-stage continuous system for producing heteropolysaccharides comprising:

(a) a fermentation stage consisting of an outer enzyme/nutrient containing chamber in which a membranous microbial growth chamber is movably mounted, said growth chamber being arranged to continuously produce *Xanthomonas campestris* cells in the near stationary growth phase and transfer polymerizing exo-enzymes and cell lysate therefrom into the surrounding medium of said enzyme/nutrient chamber and to retain said *Xanthomonas campestris* cells; and wherein said growth chamber is connected to eccentric drive means which moves said growth chamber in a manner to facilitate transfer of exo-enzymes and cell lysate therefrom into the surrounding nutrient/enzyme medium, and to produce in said growth chamber a Bernoullian presentation pressure on a forward membrane with an equal and opposite negative pressure on a rear membrane surface, thereby retaining the *Xanthomonas campestris* cells in said growth chamber; and (b) a cell-free polymerization stage consisting of at least one module to receive said exo-enzymes and cell lysate from said fermentation stage to produce said heteropolysaccharides.

2. A multi-stage continuous system according to claim 1, wherein said eccentric drive means are connectable at one of several points to said growth chamber.

3. A multi-stage contiuous system according to claim 1, wherein said eccentric drive means has variable speeds.

4. A multi-stage continuous system according to claim 1, wherein said growth chamber has a membrane at each end and said membranes are supported by membrane supports.

5. A multi-stage continuous system according to claim 1, having contacting members and said contacting members being plastic or metal and of a rigid, semi-rigid or flexible material.

6. A multi-stage continuous system according to claim 1, wherein the number of cell-free polymerizing modules making up said polymerizing stage corresponds to the length of time required to produce said heteropolysaccharides of a desired viscosity.

7. A multi-stage continuous system according to claim 1, wherein said enzyme-nutrient containing chamber is from about 5 to about 7 times as large in volume as said growth chamber.

8. A multi-stage continuous system according to claim 1, wherein said growth chamber is arranged to provide rapid and complete removal, replacement, and/or modification of the *Xanthomonas campestris* cells in said growth chamber from said fermentation stage during the continuous operation of said system.

* * * * *